(12) United States Patent
Hodge

(10) Patent No.: US 11,644,300 B2
(45) Date of Patent: *May 9, 2023

(54) DISPLACEMENT MEASURING DEVICE

(71) Applicant: ERGO FIGURE LIMITED, Warwick (GB)

(72) Inventor: Paul Hodge, Warwick (GB)

(73) Assignee: ERGO FIGURE LIMITED, Warwick (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/879,679

(22) Filed: Aug. 2, 2022

(65) Prior Publication Data

US 2022/0364843 A1  Nov. 17, 2022

Related U.S. Application Data

(63) Continuation of application No. 16/973,368, filed as application No. PCT/GB2019/051890 on Jul. 4, 2019, now Pat. No. 11,421,973.

(51) Int. Cl.
| | | |
|---|---|---|
| G01B 7/00 | (2006.01) | |
| G01B 7/16 | (2006.01) | |
| A61B 5/107 | (2006.01) | |

(52) U.S. Cl.
CPC .............. *G01B 7/18* (2013.01); *A61B 5/1072* (2013.01); *G01B 2210/58* (2013.01)

(58) Field of Classification Search
None
See application file for complete search history.

(56) References Cited

U.S. PATENT DOCUMENTS 3,937,212 A * 2/1976 Fletcher ............... A61B 5/4519
600/595
4,817,625 A * 4/1989 Miles .................. A61B 5/6831
600/595
6,142,953 A * 11/2000 Burton ................. A61B 5/1135
600/534

(Continued)

FOREIGN PATENT DOCUMENTS

DE  202015006659 U1  12/2015
EP  3558106  * 11/2017

OTHER PUBLICATIONS

International Search Report and Written Opinion dated Sep. 17, 2019 in connection with corresponding International Application No. PCT/GB2019/051890.

*Primary Examiner* — Lisa M Caputo
*Assistant Examiner* — Nigel H Plumb
(74) *Attorney, Agent, or Firm* — Stout, Uxa & Buyan, LLP; Donald E. Stout

(57) ABSTRACT

A measurement device is disclosed for measuring a change in one or more of a circumference or a perimeter of at least a portion of an object having a surface. The measurement device includes a first part for attachment to the object, a second part having a first portion moveable relative to a first portion of the first part, a determining device for determining a displacement of the first portion of the second part relative to the first portion of the first part caused by the object changing, and a biasing device for biasing the first part and the second part towards engagement. The measured displacement is for use in determining the change in one or more of a circumference or a perimeter of the object.

20 Claims, 15 Drawing Sheets

(56) References Cited

U.S. PATENT DOCUMENTS

Figure 1:
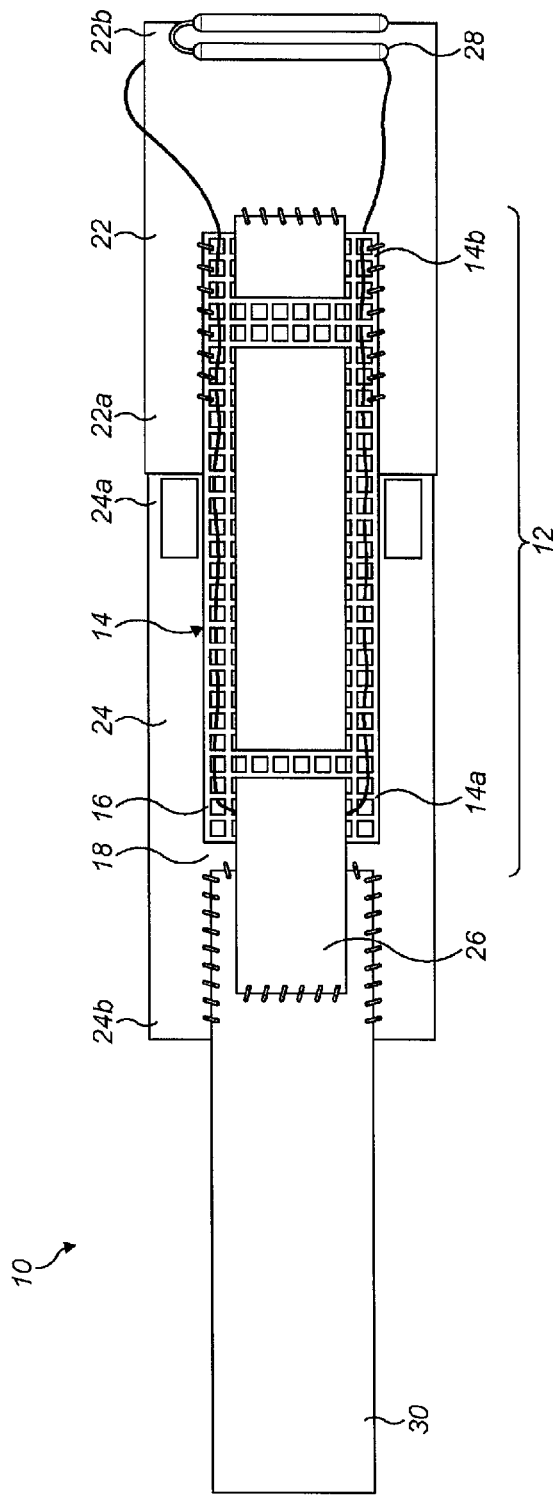

| | | | |
|---|---|---|---|
| 11,421,973 B2* | 8/2022 | Hodge | G01B 21/32 |
| 2008/0000304 A1* | 1/2008 | Nagle | G01B 7/003 |
| | | | 73/780 |

* cited by examiner

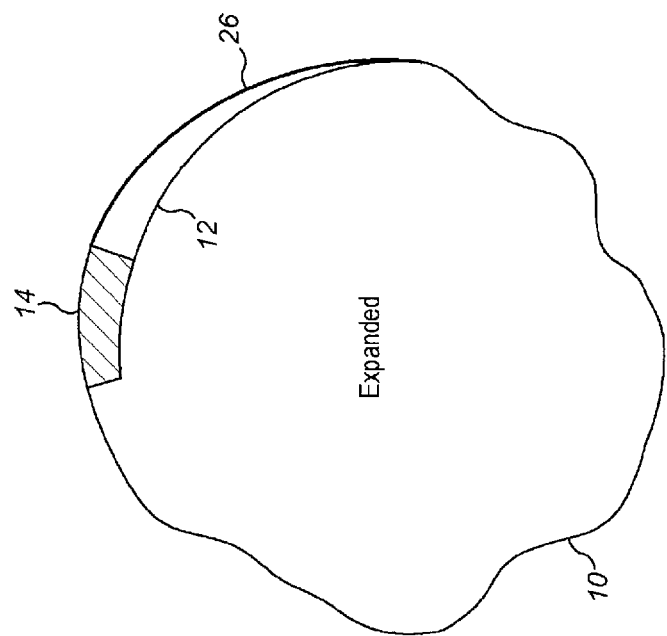
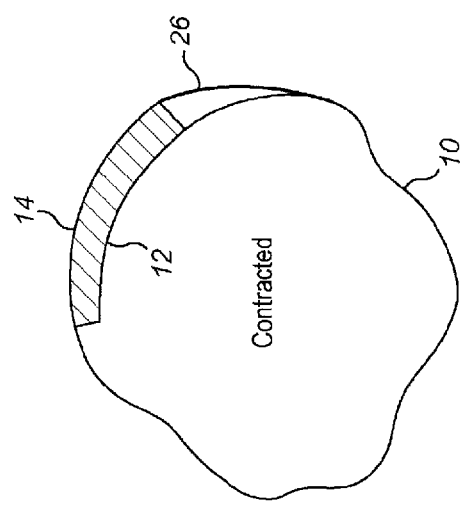
FIG. 11

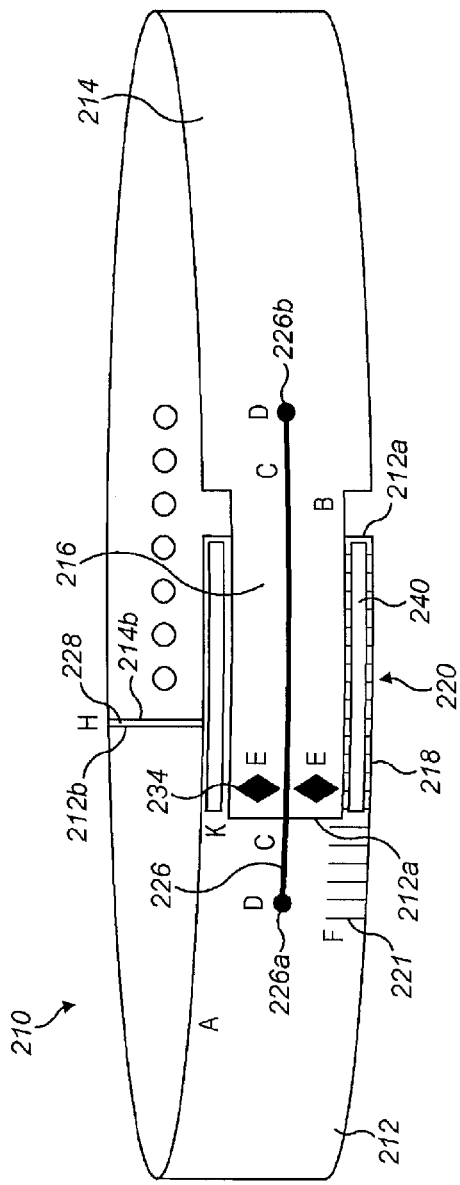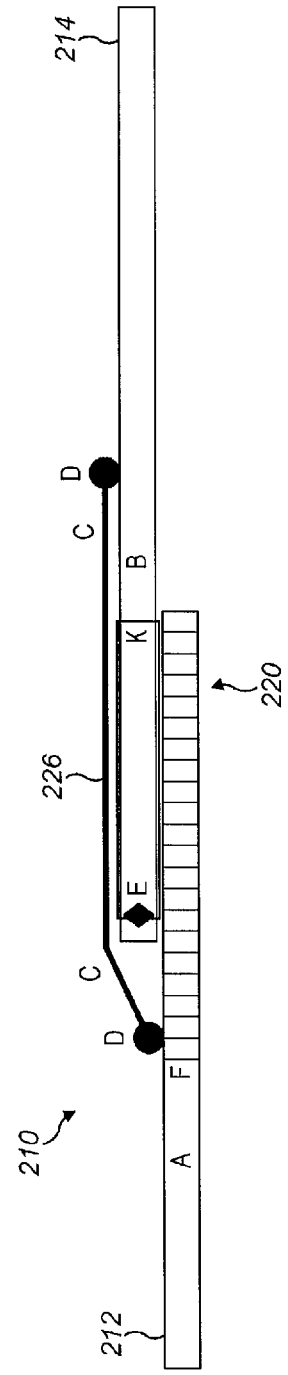

DISPLACEMENT MEASURING DEVICE

This application is a continuation under 35 U.S.C. 120 of U.S. patent application Ser. No. 16/973,368, entitled Displacement Measuring Device, and filed on Dec. 8, 2020, now allowed, which in turn is a national phase application under 35 U.S.C. 371 of International Application No. PCT/GB2019/051890, filed on Jul. 4, 2019. Application Ser. No. 16/973,368 also claims priority to UK Application No. 1811050.2, filed on Jul. 5, 2018. All of the foregoing applications are herein expressly incorporated by reference, in their entirety.

DESCRIPTION OF INVENTION

The present invention relates to a measurement device. More particularly, but not exclusively, the present invention relates to a measurement device for measuring a change in the size and/or shape of an object.

In the art, measurement devices are known for measuring an object, for example, its height or length. However, such measurement devices are typically difficult and/or require substantial effort to use in relation to objects which have an irregular surface, and/or have curved surfaces, for example. For example, measuring the size and/or shape of parts of a plant, animal and/or human can be difficult. Furthermore, monitoring changes in the size and/or shape of such parts can be challenging, e.g. monitoring changes over time.

For example, in the case of humans, manual measurement of body parts is often required to monitor changes in, for example, a person's waist, or the range of a person's movement, e.g. flexion or extension between body parts. Such changes can be important for treating and/or diagnosing certain medical conditions. The person that requires such monitoring may not be able to perform a manual measurement due to ill health, for example, and so a third person is required, often a health professional. This can be expensive and/or cause delays in identifying symptoms caused by a deterioration of a person's condition that may not be immediately apparent to the person.

According to embodiments we provide a measurement device for measuring a change in the size and/or shape of at least a portion of an object having a surface, the device including:
a first part for attachment to the object;
a second part having a first portion moveable relative to a first portion of the first part; and
a determining device for determining a displacement of the first portion of the second part relative to the first portion of the first part caused by the object changing, wherein the displacement is for use in measuring the change in the size and/or shape of the object.

Optionally at least the first portion of the first part is positioned above or below the first portion of the second part.

Optionally the determining device is provided on at least one of the first and second parts.

Optionally the first and second parts are connected.

Optionally the second part has a second portion which is fixed against movement relative to the first part.

Optionally the first portion of the second part is slidingly connected to the first part.

Optionally at least the first portion of the second part is biased towards the first part and optionally or preferably the first and second parts are biased towards engagement with the object when the measurement device is attached thereto.

Optionally at least the first portion of the second part is biased towards engagement with the first part.

According to embodiments we provide a measurement device for measuring a change in the size and/or shape of at least a portion of an object having a surface, the measurement device including:
a first part for attachment to the object, wherein the first part includes a first portion and a second portion which are configured to permit relative movement between them when the object changes;
a determining device for determining a relative displacement of the first and second portions caused by the object changing,
wherein the displacement is for use in measuring the change in the size and/or shape of the object.

Optionally the measurement device is configured to be self-supported relative to the object during use to measure the change during normal operation.

Optionally, during use, the measurement device may change from a first condition, corresponding to an initial size/shape of the object, to a second condition, corresponding to a subsequent size/shape of the object after the object has changed, wherein the determining device directly determines the relative displacement between the first portion of the first part relative to the first portion of the second part/second portion of the first part.

Optionally the first part is configured such that, when attached to the object, the first part increases in length when the object increases in size/changes shape in a first direction, and decreases in length when the object decreases in size/changes shape in a second direction.

Optionally the first portion of the first part is biased towards the first portion of the second part/second portion of the first part in use such that when the object increases in size/changes in shape in a first direction, the relative displacement increases, and when the object decreases in size/changes in shape in a second direction, the relative displacement decreases.

Optionally the first portion of the first part is biased towards the first portion of the second part/second portion of the first part in use such that, when the object increases in size/changes shape in a first direction, the relative displacement increases, and when the object decreases in size/changes shape in a second direction, the relative displacement decreases.

Optionally the first portion of the first part moves away from the first portion of the second part/second portion of the first part in use when the object increases in size/changes shape in a first direction, and the first portion of the first part moves towards the first portion of the second part/second portion of the first part when the object decreases in size/changes shape in a second direction.

Optionally embodiments include one or more of the following:
a) the respective first portions, or the first and second portions of the first part, are biased against relative movement between them; and
b) optionally or preferably, the respective portions, or the first and second portions of the first part, at least partially overlap.

Optionally the determining device includes a first element provided on one of the first and second parts/portions, and a second element provided on the other one of the first and second parts/portions, wherein the first and second elements may co-operate to determine the displacement.

Optionally the determining device includes an electric circuit connectable to a power supply of the measurement device and wherein the electric circuit has a variable resistance which increases or decreases in correlation to the displacement.

Optionally the first and second elements co-operate to form the electric circuit.

Optionally the determining device includes sensor devices.

Optionally the electric circuit includes a plurality of resistors, and wherein the first and second elements co-operate to vary the number of resistors connected in the electric circuit when the first portion of the second part moves relative to the first portion of the first part such that the resistance of the electric circuit is correlated to the displacement.

Optionally the first part/portion, and/or second part/portion, are deformable to follow the surface of the object as it changes during use, optionally or preferably the parts/portions are resiliently deformable.

Optionally the first part includes an engagement surface, which, in use, remains in steadfast engagement with the surface of the object as the object changes.

Optionally the measurement device is configured as a band or strap and optionally or preferably end portions of the first part are connected together to form the band or strap.

Optionally the first part is configured to increase/decrease in length during use in accordance with the change in size or shape of the object, and/or optionally the relative displacement increases or decreases in accordance with the change in shape of the object during use when the object changes size or shape.

Optionally the first part is releasably attachable to the object.

Optionally embodiments include an attachment device for attaching the first part to the object.

Optionally the first part includes first and second members.

Optionally the first and second members are connected by the attachment device.

Optionally the first and second members are permitted move relative to one another when the object changes.

Optionally the measurement device is configured as a user wearable device for attachment to a portion of a user's body to measure changes in said portion.

Optionally embodiments include one or more or all of the following features:
a) a processor;
b) memory for storing instructions and/or data for processing by the processor; and
c) communication link for communicating with a computing device,
wherein features a) to c) are optionally or preferably arranged to operate the determining device to obtain the displacement, and optionally or preferably communicate said displacement to a computer device at predetermined intervals.

In another aspect of the invention, there is provided a measurement device for measuring a change in one or more of a circumference or a perimeter of at least a portion of an object having a surface. The measurement device includes a first non-elastic elongate band for attachment to the object and a second non-elastic elongate band having a first portion moveable relative to a first portion of the first non-elastic elongate band, wherein the first and second non-elastic elongate bands are formed of non-compliant material and are biased towards one another by a biasing device which overlaps each of the first portions and connects the non-elastic elongate bands together. The measurement device further comprises a determining device for determining a displacement of the first portion of the second non-elastic elongate band relative to the first portion of the first non-elastic elongate band caused by the object changing, wherein the displacement is for use in measuring the change in the one or more of the circumference or the perimeter of the object.

In some embodiments of the invention, at least the first portion of the first non-elastic elongate band is positioned above or below the first portion of the second non-elastic elongate band. The determining device is provided on at least one of the first and second non-elastic elongate bands. The first and second non-elastic elongate bands may be connected. The second non-elastic elongate band may have a second portion which is fixed against movement relative to the first non-elastic elongate band, or wherein the first portion of the second non-elastic elongate band is slidingly connected to the first non-elastic elongate band.

In some embodiments, at least the first portion of the second non-elastic elongate band is biased towards the first non-elastic elongate band and/or the first and second non-elastic elongate bands are biased towards engagement with the object when the measurement device is attached thereto. In certain embodiments, at least the first portion of the second non-elastic elongate band is biased towards engagement with the first non-elastic elongate band.

A raised track or casing may be provided at the first portion of the first non-elastic elongate band to allow the first portion of the second non-elastic elongate band to run along the first portion of the first non-elastic elongate band without slippage or twisting.

In yet another aspect of the invention, there is provided a measurement device for measuring a change in one or more of a circumference or a perimeter of at least a portion of an object having a surface. The measurement device includes a first non-elastic elongate band for attachment to the object, wherein the first non-elastic elongate band includes a first non-compliant portion and a second non-compliant portion which are configured to permit relative movement between them when the object changes. The measurement device further comprises a determining device for determining a relative displacement of the first and second portions caused by the object changing, wherein the displacement is for use in measuring the change in one of more of the circumference or the perimeter of the object.

The aforementioned measurement device may include one or more of the following:
a) the respective first portions of the first and second non-elastic elongate bands, are biased against relative movement between them; and
b) optionally or preferably, the respective portions of the first and second non-elastic elongate bands, at least partially overlap.

The determining device may include a first element provided on one of the first and second non-elastic elongate bands/portions, and a second element provided on the other of the first and second non-elastic elongate bands/portions, wherein the first and second elements may cooperate to determine the displacement. It may also include an electric circuit connectable to a power supply of the measurement device, wherein the electric circuit has a variable resistance which increases or decreases in correlation to the displacement. The determining device includes an electric circuit connectable to a power supply of the measurement device and the electric circuit has a variable resistance which increases or decreases in correlation to the displacement, and further wherein the first and second elements cooperate to form the electric circuit. The electric circuit further includes a plurality of resistors, and wherein the first and second elements co-operate to vary the number of resistors connected in the electric circuit when the first portion of the second non-elastic elongate band moves relative to the first portion of the first non-elastic elongate band such that the resistance of the electric circuit is correlated to the displacement.

Additionally, the first non-elastic band/portion, and/or second non-elastic band/portion, are deformable to follow the surface of the object as it changes during use, the non-elastic bands/portions are resiliently deformable, and/or wherein the first non-elastic band includes an engagement surface, which, in use, remains in steadfast engagement with the surface of the object as the object changes.

The measurement device may be configured as a band or strap, and optionally or preferably end portions of the first non-elastic elongate band are connected together to form the band or strap. The first non-elastic elongate band may be configured to increase or decrease in length during use in accordance with the change in size or shape of the object, and/or optionally or preferably the relative displacement increases or decreases in accordance with the change in shape of the object during use.

The first non-elastic elongate band may be releasably attachable to the object, and/or may include an attachment device for attaching the first non-elastic elongate band to the object. The measurement device may also be configured as a user wearable device for attachment to a portion of a user's body to measure changes in said portion, and/or wherein the measurement device includes one or more or all of the following features:
  a) a processor;
  b) memory for storing instructions and/or data for processing by the processor; and
  c) communication link for communicating with a computing device,
  wherein features a) to c) are arranged to operate the determining device to obtain the displacement, and/or communicate the displacement to a computer device at pre-determined intervals and/or as instructed by the computing device.

In still another aspect of the invention, there is provided a measurement device for measuring a change in one or more of the circumference or perimeter of at least a portion of an object having a surface. The measurement device includes a first part for attachment to the object, a second part having a first portion moveable relative to a first portion of the first part, and a raised track or casing provided at the first portion of the first part to allow the first portion of the second part to run along the first portion of the first part without slippage or twisting. The measurement device additionally includes a determining device for determining a displacement of the first portion of the second part relative to the first portion of the first part caused by the object changing, wherein the displacement is for use in measuring the change in the one or more of the circumference or perimeter of the object. In certain embodiments, the measurement device may be utilized for measuring a change in one or more of the circumference or perimeter of at least a portion of a user's ankle, foot or lower limb.

Figure 2:
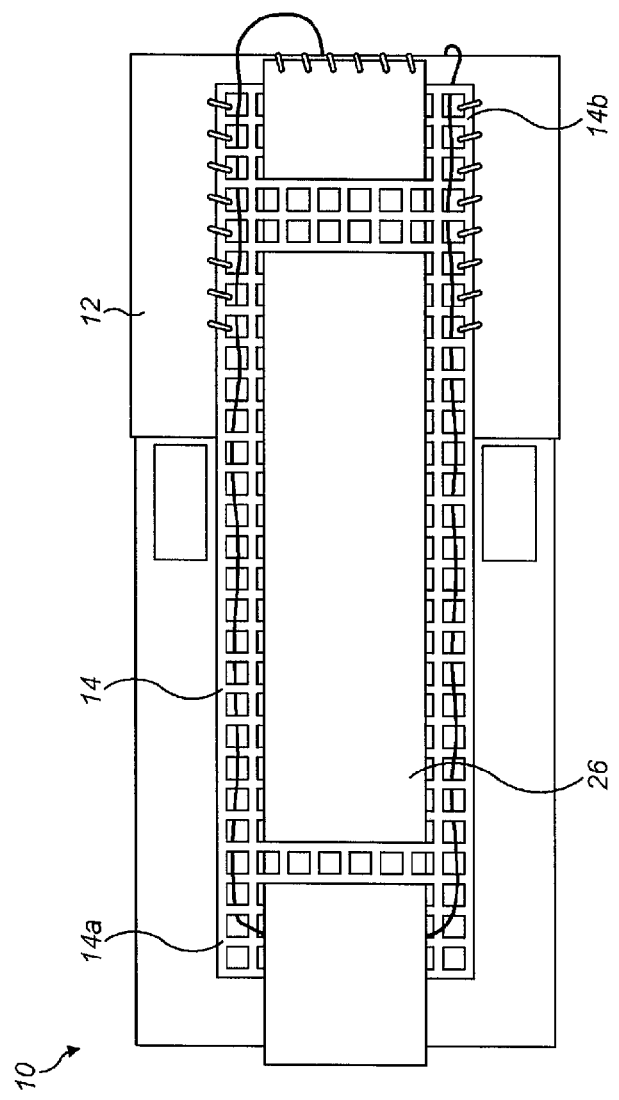
Figure 3:
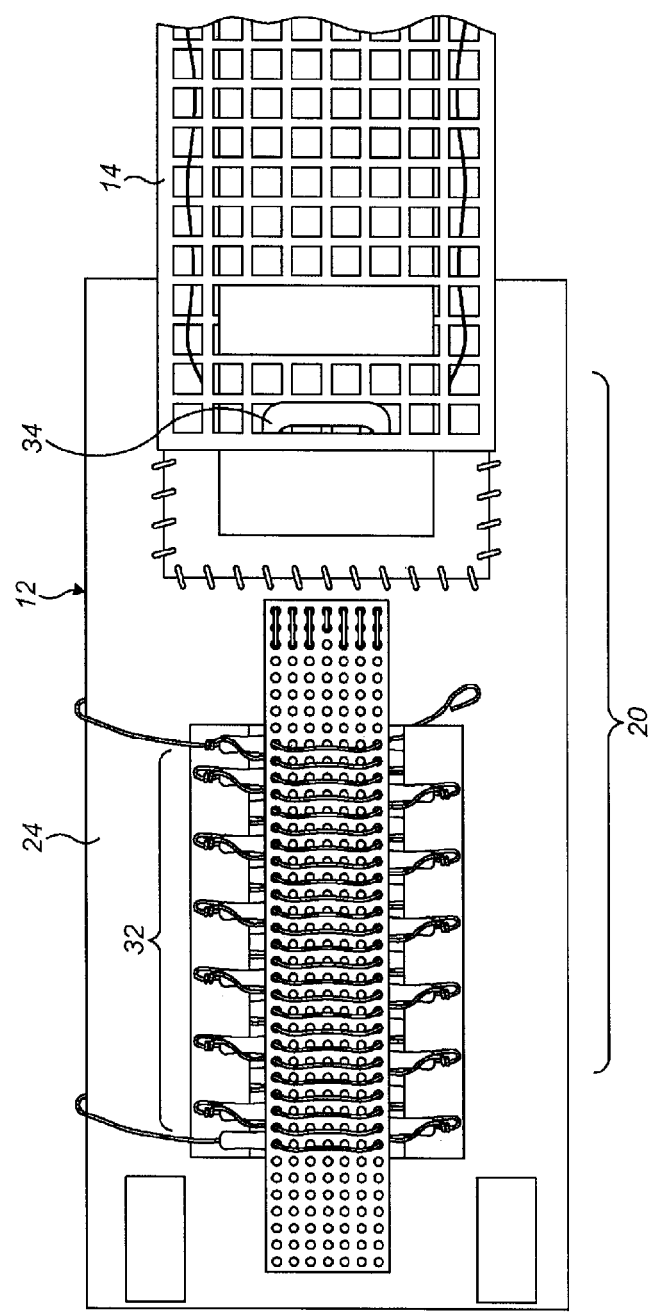
Figure 4:
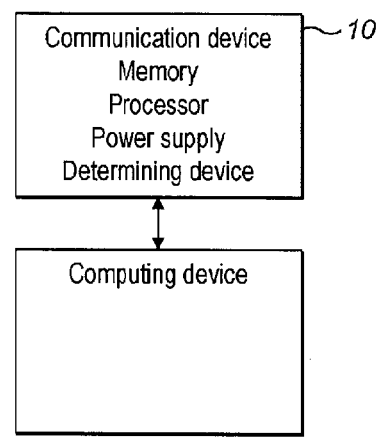
Figure 5:
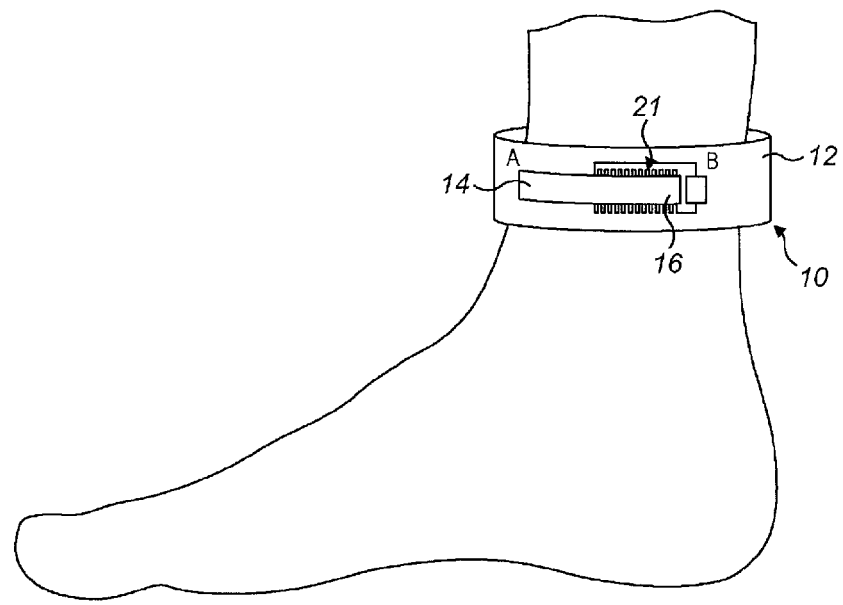
Figure 6A:
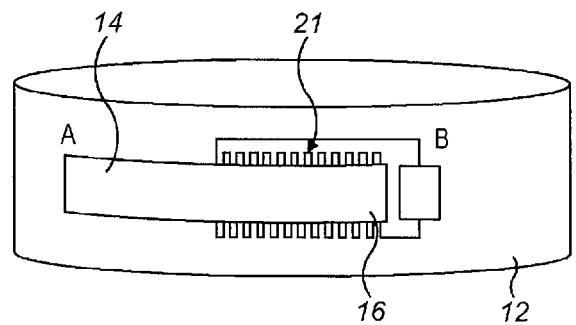
Figure 6B:
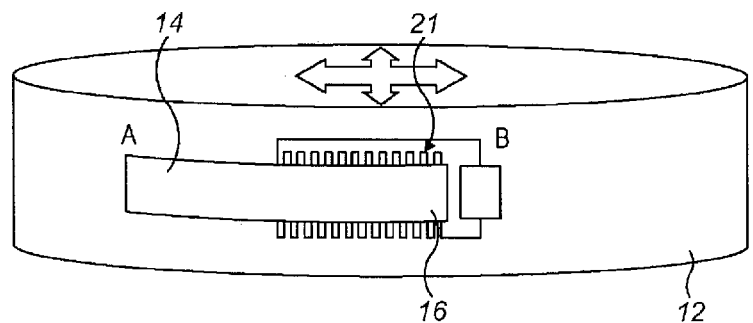
Figure 6C:
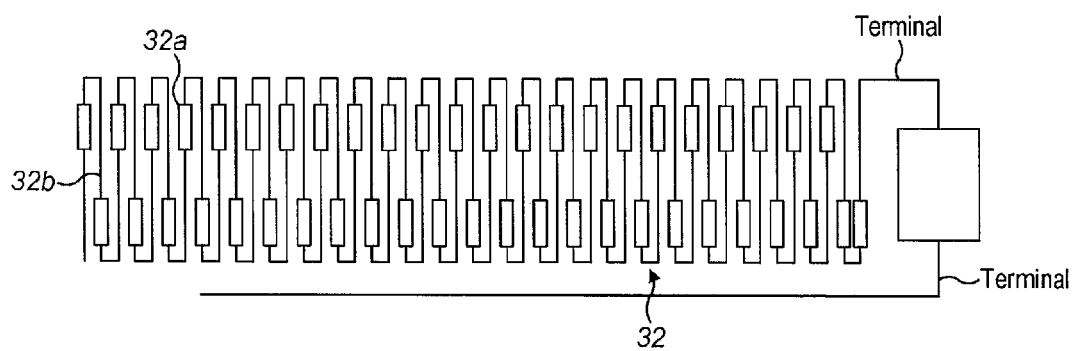
Figure 7A:
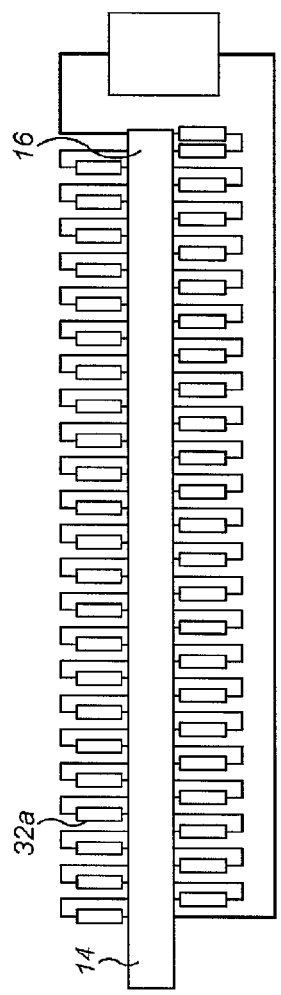
Figure 7B:
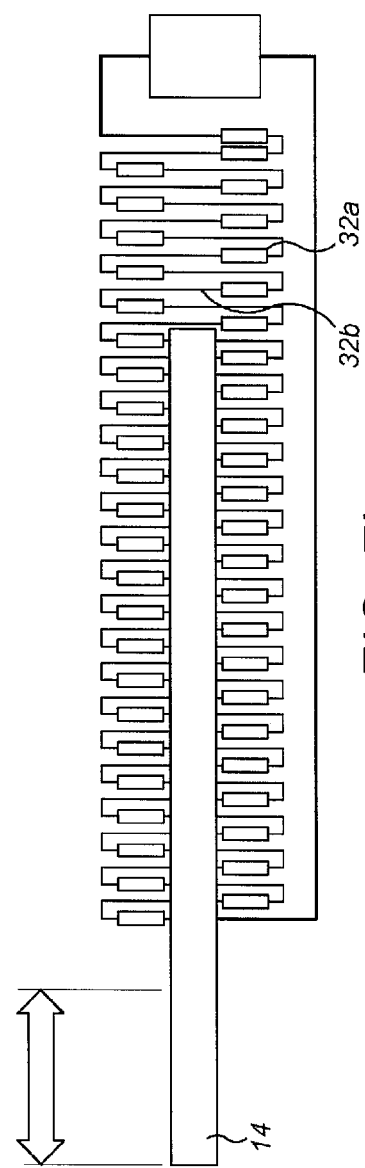
Figure 8A:
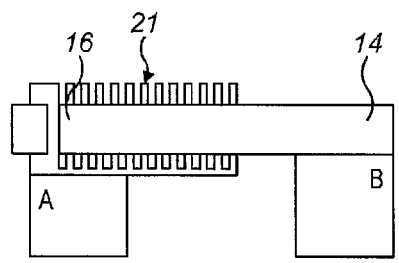
Figure 8B:
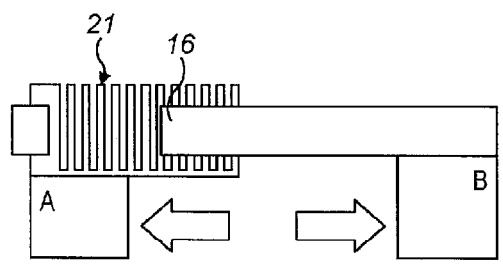
Figure 9A:
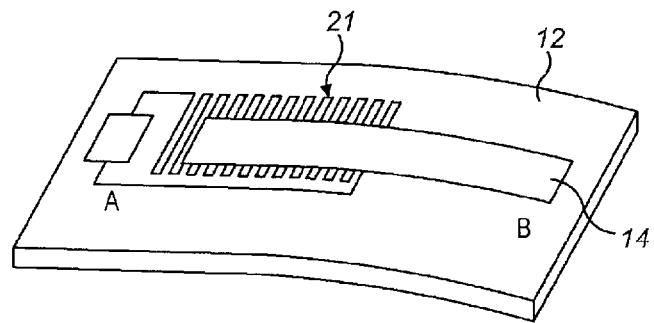
Figure 9B:
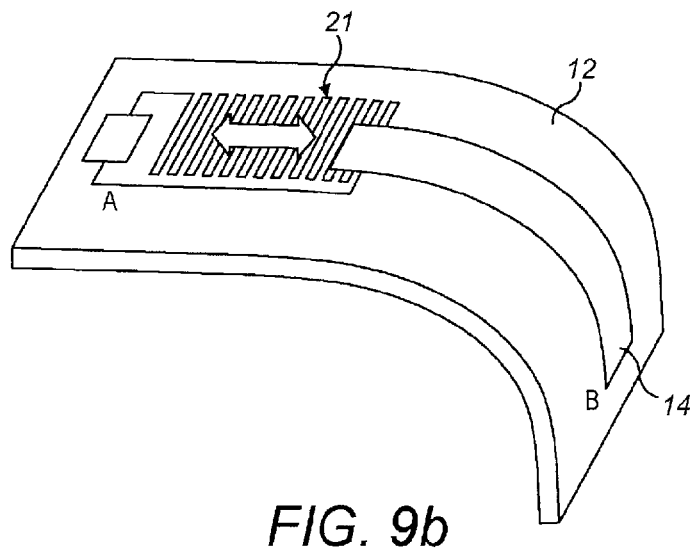
Figure 10A:
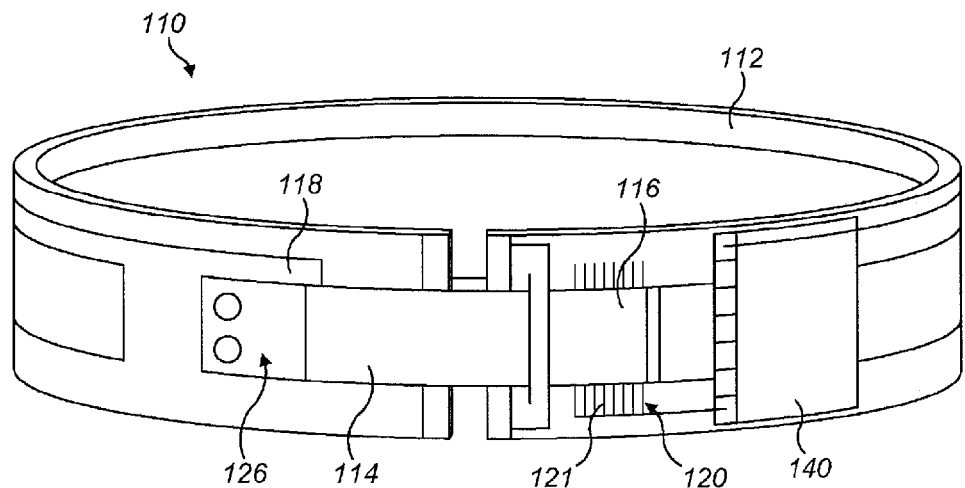
Figure 10B:
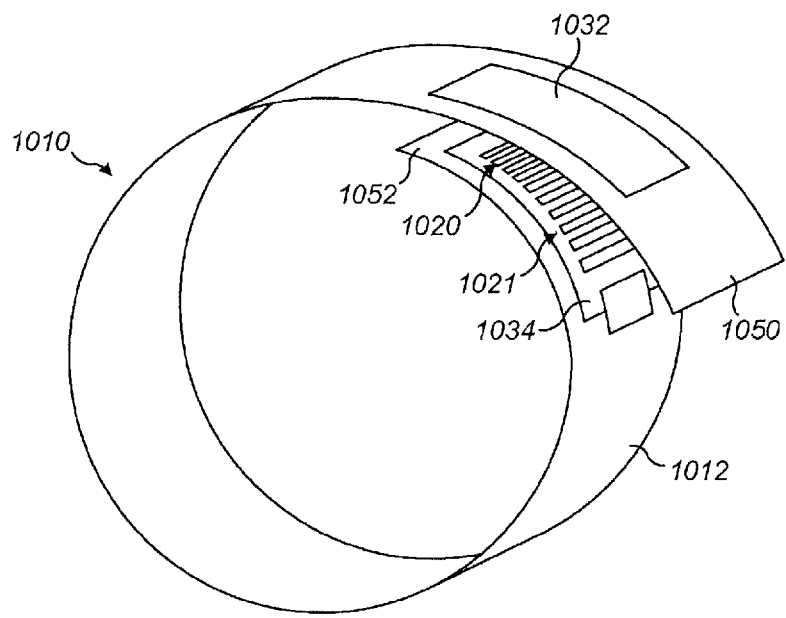
Figure 13A:
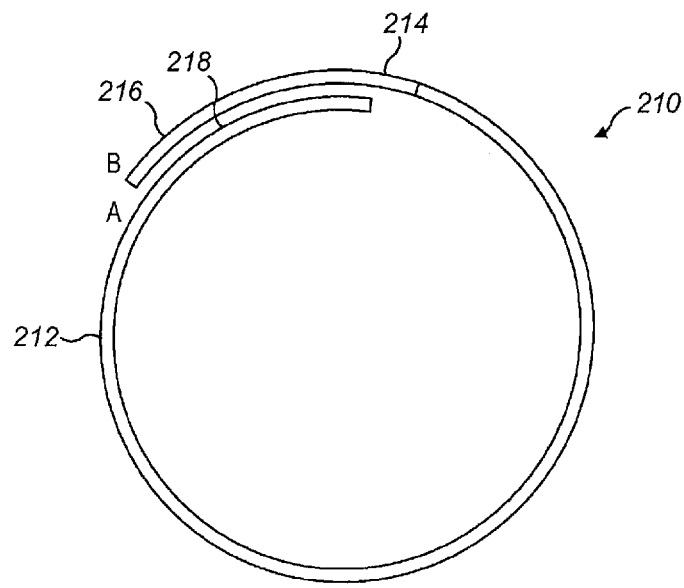
Figure 13B:
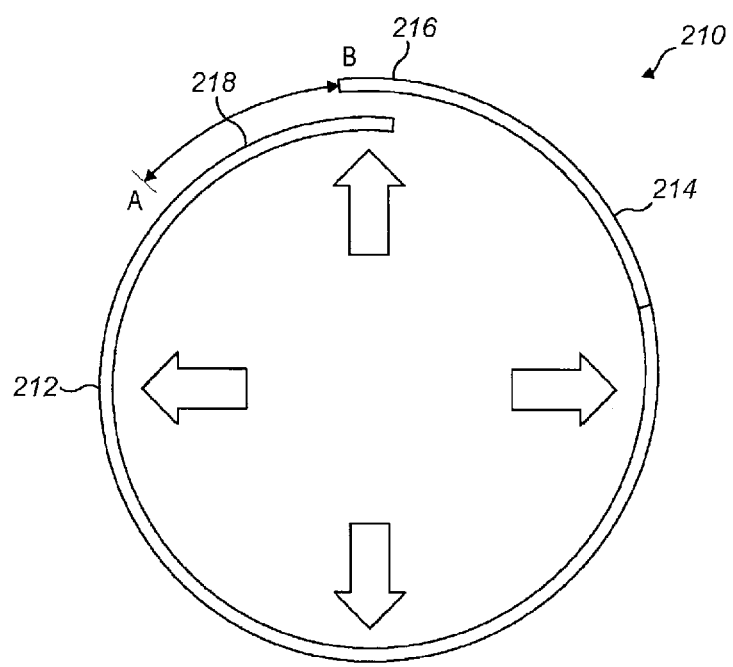
Figure 14A:
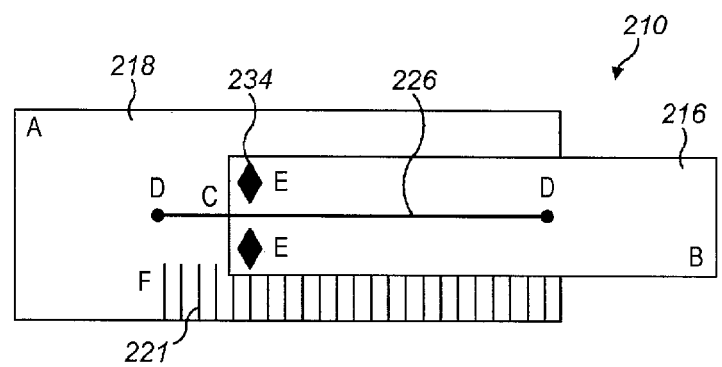
Figure 14B:
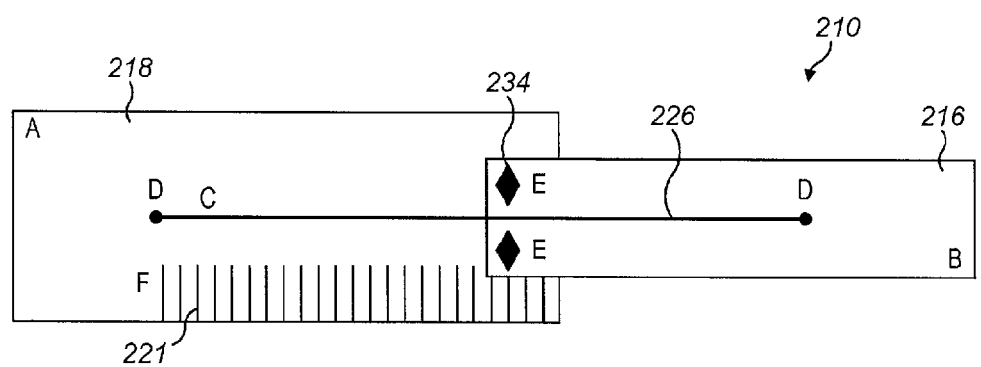
Figure 15A:
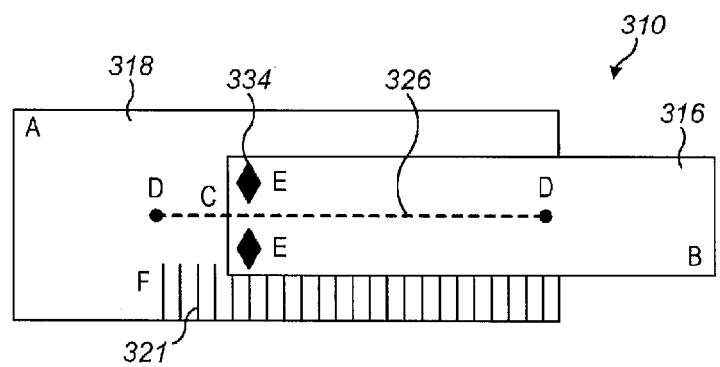
Figure 15B:
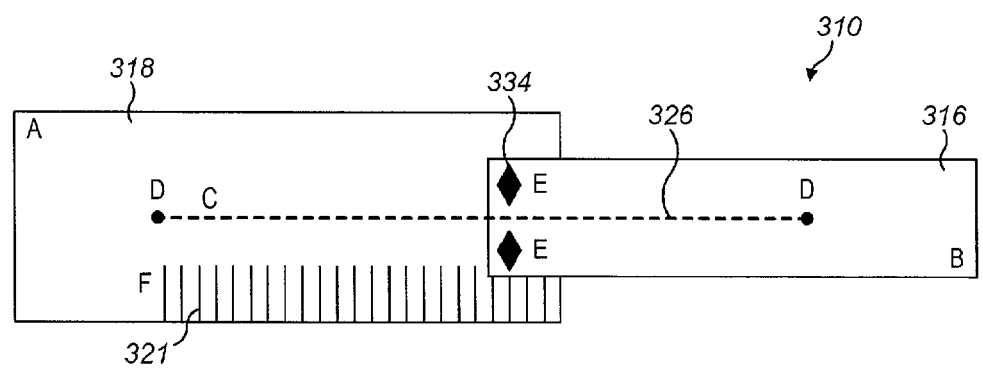
Figure 16A:
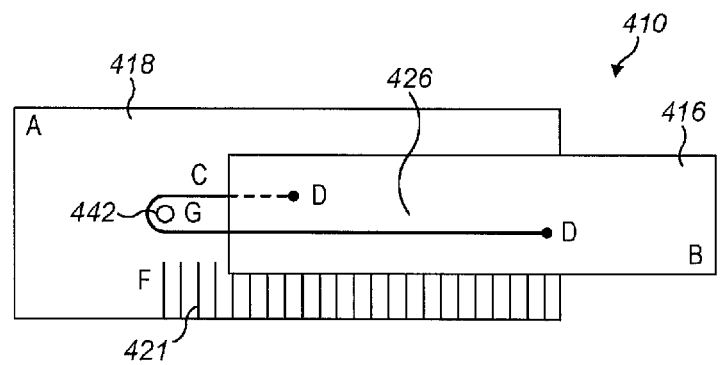
Figure 16B:
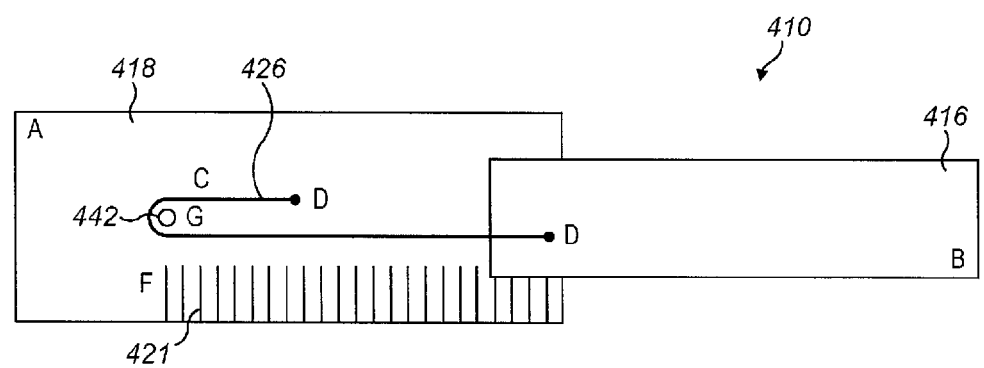
Figure 17A:
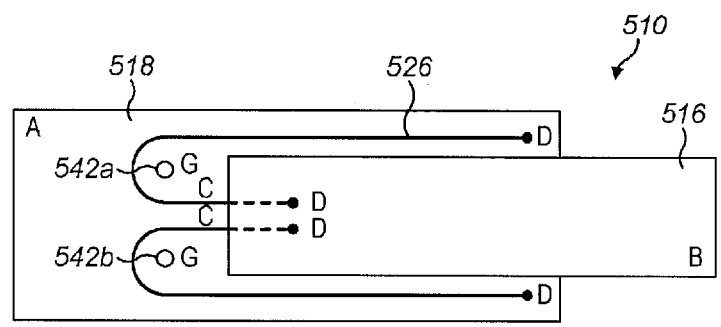
Figure 17B:
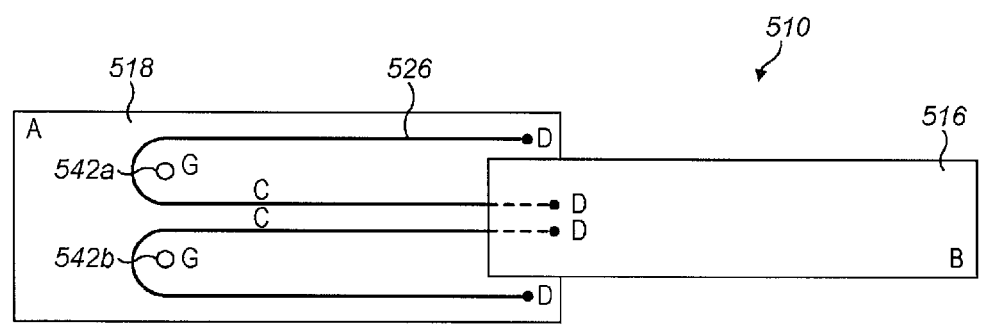

Embodiments of the invention will be set out below by way of example only with reference to the accompanying figures, of which:
  FIG. 1 is a plan view of a measurement device in accordance with the present invention in a first configuration;
  FIG. 2 is a plan view of the measurement device of FIG. 1 in a second configuration;
  FIG. 3 is a plan view showing certain component parts of the measurement device of FIG. 1;
  FIG. 4 is a schematic diagram of the measurement device of FIG. 1;
  FIG. 5 is a schematic diagram of the measurement device of FIG. 1 in use for a particular application thereof;
  FIGS. 6a and 6b are schematic diagrams of the measurement device of FIG. 1 in respective use conditions;
  FIG. 6c is a schematic diagram of certain component parts of the measurement device of FIG. 1;
  FIGS. 7a and 7b are schematic diagrams of certain component parts of the measurement device of FIG. 1 in the use conditions shown in FIGS. 6a and 6b respectively;
  FIGS. 8a and 8b are schematic diagrams of certain component parts of the measurement device according to embodiments in respective use conditions for a particular application;
  FIGS. 9a and 9b are schematic diagrams of certain component parts of the measurement device according to embodiments in respective use conditions for a particular application;
  FIGS. 10a and 10b show further respective measurement devices according to embodiments;
  FIG. 11 is a schematic diagram showing certain aspects of a measurement device which is shown in plan cross-sectional views according to embodiments in respective use conditions for a particular application;
  FIGS. 12a and 12b show a measurement device according to an embodiment of the invention;
  FIGS. 13a and 13b are schematic diagrams of the measurement device of FIGS. 12a and 12b in respective use conditions;
  FIGS. 14a and 14b are schematic diagrams of the measurement device of FIGS. 12a and 12b in respective use conditions;
  FIGS. 15a and 15b show a measurement device according to an embodiment of the invention;
  FIGS. 16a and 16b show a measurement device according to an embodiment of the invention; and
  FIGS. 17a and 17b show a measurement device according to an embodiment of the invention.

With reference to FIGS. 1, 2 and 3, a measurement device 10 in accordance with embodiments of the present invention is shown in first and second configurations respectively. The measurement device 10 is for measuring a change in the size and/or shape of at least a portion of an object having a surface.

In embodiments, the measurement device 10 includes a first part 12 for attachment to an object and a second part 14. The second part 14 has a first portion 16 moveable relative to a first portion 18 of the first part 12. The measurement device 10 includes a determining device 20 (see FIG. 3) for determining a displacement of the first portion 16 relative to the first portion 18 as will be described in more detail below. The measurement device 10/first part 12 is configured for secure or steadfast engagement with the object such that the first part/measurement device 10, when attached, remains attached to the object whilst the object changes to maintain accurate measurement of any changes in size or shape thereof. The first portions 16, 18 and/or first and second parts 12, 14 can move relative to each other whilst the first part 12 is attached to the object. In embodiments, the first and second parts 12, 14 are configured to move relative to one another so that the displacement between them/the respective portions 16, 18 increases and decreases when the object increases and decreases in size respectively whilst the first part 12 is attached to the object. The movement of the first and/or second parts 12, 14 may be in a direction along the surface of the object during use. The displacement is for use in measuring the change in the size and/or shape of the object. The measurement device 10 is for measuring such changes in situ, i.e. whilst attached to the object. The measurement device 10 is configured to remain in place, i.e. it is self-supported without user intervention once the measurement device 10 has been attached to the object, to measure such changes during normal operation, functioning or movement of the object to provide a continuous monitoring ability without interfering with the object's operation, functioning or movement. In embodiments, the first portions 16, 18 thus move relative to one another in accordance or correspondence with changes in the size or shape of the object. Hence, if the size increases or the shape changes in a first direction, the relative displacement between the first portions 16, 18 increases, and if the size decreases or the shape changes in a second direction, the relative displacement between the first portions 16, 18 decreases.

In embodiments, the measurement device 10 may measure a change in one or more of a circumference, perimeter, width, height or depth of an object for example. The change in displacement may be used to correlate to a change in volumetric or surface area of the object in embodiments if the original shape or volume of the object before the change occurred is known, for example.

In embodiments, the measurement device 10 is configured as a user wearable device such that a user may attach the device and wear the device on his or her person.

In embodiments, the first part 12 is formed from a flexible material. The materials may include plastic, leather and or rubber. The first part 12 may be deformable to adopt a suitable shape when the first part is attached to the surface of an object such that an engagement surface of the first part 12 abuts and/or follows the shape/surface of the object. The first part 12 may deform to the shape/surface of the object to which it is attached.

The first part 12, in embodiments, is a generally elongate member that may be deformed to create various shapes, e.g. a partial or wholly annular shape. The first part 12 may be a generally planar member. FIG. 2 shows the first part 12 configured as an annular shape for attachment to an object having an annular surface. The first part 12 may adopt other shapes in accordance with the object to which it is attached in embodiments. For example, the first part 12 may not form a closed shape but another formation which is not closed, e.g. the first part 12 may be configured or deformed to form a V-shape or L-shape. In embodiments, the first part 12 may be substantially planar. In embodiments, the first part 12 may include operative portions or ends which include operative component parts of the device 10, e.g. component parts of the determining device 20 and/or the second part 14.

As shown in the FIGS. 1 to 3, in embodiments, the first part 12 may include include first and second members 22, 24 which are each attachable to the object. The first and second members 22, 24 may each be in the form of generally elongate members. The first and second members 22, 24 may have respective operative ends 22a, 24a, and distal ends 22b, 24b. The operative ends 22a, 24a may include operative component parts of the determining device 20 as will be described.

The first and second members 22, 24 may be connected together to permit relative movement between them and/or relative movement between the operative ends 22a, 24a. The first and second members 22, 24, in embodiments for which they are connected, may be generally aligned with each other in plan view. The first and second members 22, 24 may be connected together by a biasing device 26 that biases the first and second members 22, 24/operative ends 22a, 24a against relative movement. In embodiments, the biasing device 26 is a resiliently deformable member which may be made from an elastic material and/or be configured as a band which is attached at its ends to the first and second members 22, 24 respectively. In embodiments, the biasing device 26 extends over the outer surfaces of the first and/or second parts 22, 24 so as to urge the part(s) into engagement with the object when the measurement device 10 is attached thereto whilst permitting relative movement between the parts 22, 24/operative ends 22a, 24a.

The measurement device 10 may include an attachment device 28 for providing the attachment of the measurement device 10/first part 12 to the object. The attachment device 28 secures the measurement device 10 to the object to hold the measurement device 10 so that the device is self-supported during use, i.e. during changes in the size/shape of the object. The attachment device 28 may releasably connect respective ends of the first part 12 so that the first part 12 may be fastened to an object. In embodiments, the attachment device 28 may include a strap 30 which is connected, at one end, to an end portion of the first part 12, e.g. its distal end, and, which has an opposite free end which may be releasably connected to an opposite end portion, e.g. its opposite distal end, of the first part 12. The attachment device 28 may include any form of fastening or attachment means sufficient to hold the measurement device 10 relative to the object, e.g. a buckle, or hook and loop fastener, to couple the respective ends of the first part 12 together. For example, in embodiments for which the first part 12 includes first and second members 22, 24, the distal end 22b may include a buckle and the distal end 24b may include a strap 30 which may be fastened together to hold the first part 12 to an object.

The second part 14 is connected to the first part 12 in embodiments. In embodiments, the second part 14 may be provided on a surface of the first part 12 which does not engage the object during use, i.e. the surface faces outwardly away from the object to which the first part 12 is attached during use. In embodiments, the first portion 16 of the second part 14 is slidingly connected to the first part 12 in the sense that the first portion 16 will slide over the outward surface of the first part 12 when the first part 12 moves, deforms or otherwise extends or contracts in length during use. The second part 14 may lie above the first part 12 in embodiments.

In embodiments, the second part 14 may be a generally elongate member, and/or may have first and second end portions 14a, 14b. The second part 14 may be a generally planar member. In embodiments, the second end portion 14b is connected to the first part 12 by a fixed connection to prevent relative movement therebetween. The first end portion 14a may be connected to the first part 12 so that it is free to move relative to first part 12, e.g. the first end portion 14a may move along the top or outward surface of the first part 12. In embodiments, the second part 14 may be made from a flexible or deformable material. The material may include plastic. The material is relatively inextensible but may be resiliently deformable in embodiments. In embodiments, the first portion 16 may be provided adjacent or at the first end portion 14a. In embodiments for which the first part 12 includes first and second members 22, 24, the second part 14 may be connected so that the second part 14 is fixed to the first member 22 whilst the second part 14 may be free to move relative to the second member 24. In such embodiments, the second part 14 extends from the first member 22 to the second member 24, e.g. the second part 14 may overlie or overlap the second member 24. The first portion 16 may be provided at a section, e.g. the first end portion 14a, of the second part 14 which is free to move relative to the second member 24.

In embodiments, the first portion 16 and/or first end portion 14a may be biased towards engagement with the outward surface of the first part 12 such that the first portion 16 follows any changes in the shape/size of the first part 12 to stay engaged therewith. In embodiments for which a biasing device 26 is provided, the biasing device 26 may bias the first portion 16/first end portion 14a towards engagement. In embodiments for which the first part 12 is a single member, biasing device 26 may be provided to connect the second part 14 to the first part 12 only (rather than to connect respective members of the first part 12 together as in certain embodiments) so that it biases the second part 14 towards engagement with the first part 12 such that the second part 14 follows any changes in the shape/size of the first part 12.

It will be appreciated that in variously described embodiments the second part 14 is thus configured to deform and follow any changes in the shape/size of the first part 12 caused by deformation thereof during use. FIG. 1 shows the measurement device 10 in a first condition in which it is in an open configuration lying on a flat surface. FIG. 2 shows the measurement device 10 in a second condition in which it is in an annular, closed, configuration. It can be seen that the first and second parts 12, 14 are in close engagement for both configurations.

With reference to FIG. 3, this shows the determining device 20 as provided in certain embodiments. The second part 14 is shown in an open state so that its lower surface, i.e. the surface which faces the outer surface of the first part 12, is visible, so that certain elements of the determining device 20 can be seen.

In embodiments, the determining device 20 includes a first element 32 provided on the first part 12 and a second element 34 provided on the second part 14. In embodiments for which the first part 12 includes first and second members 22, 24, the first element 32 is provided on the second member 24. The first and second elements 32, 34 may co-operate to determine any relative displacement between the first portions 16, 18 as will be described. In embodiments, the determining device 20 includes an electric circuit 21 having a variable resistance which increases or decreases in correlation to the displacement. In embodiments, the first and second elements 32, 34 co-operate to form parts of the electric circuit 21. The determining device 20 may include a power supply for supplying power to the electric circuit 21. The power supply may be a battery or the like. The measurement device 20 may include a switch operable by the processor to supply power to the electric circuit 21. As will be described, in embodiments, the first and second elements 32, 34 co-operate to vary the resistance of the electric circuit 21 when the first portion 16 of the second part 14 moves relative to the first portion 18 of the first part 12 such that the resistance of the electric circuit 21 is correlated to the displacement.

For certain embodiments, the first element 32 includes a plurality of resistors 32a connected in series and which are provided on an outer surface of the first part 12. The resistors 32a are connected by respective wire portions 32b such that wire portions 32b which connect adjacent resistors 32a are each exposed to permit electrical connection thereto. The resistors 32a are electrically connected to a first terminal of the power supply. In embodiments, the resistors 32a are provided on a flexible circuit substrate so that they follow the changes in shape of the first part 12 during use. In embodiments, the resistors 32a may each be separated by a constant distance.

For certain embodiments, the second element 34 includes an electrical contact (not shown). In embodiments, the electrical contact (not shown) is provided on an inwardly facing surface of the second part 14 which faces the outer surface of the first part 12. The electrical contact (not shown) is electrically connected to a second terminal of the power supply. When the electrical contact (not shown) is in contact with one of the wire portions 32b, the electric circuit 21 is completed so that current flows from the power supply and through the resistors 32a. If there is no contact, the circuit 21 is open and no current flows. FIG. 4 shows certain component parts that may be incorporated and/or communicate with the measurement device 10 in embodiments. For example, the measurement device 10 may include a communication device for transmitting information or data from the measurement device to a computing device, e.g. a remote computing device, and/or receiving information, data, operating instructions from a computing device to operate the measurement device 10. The computing device may be a cellular telephone with smart capability, a tablet, a laptop or an electronic watch with smart capability. The communication device may take any suitable form known in the art to permit communication with a computing device. For example, the communication device may include radio circuitry to permit communication over Wi-Fi, Bluetooth, or telecommunication networks to connect with a remote computing device. The measurement device 10 may include a processor and/or memory for operating the various parts of the device 10 and storing information/data therefrom. The term processor may denote any control circuitry that is operable to control operation of the measurement device 10 and which circuitry may not include memory in embodiments. The measurement device 10 may include a current meter that may be operated by the processor to determine the amount of current flowing through the electric circuit 21, for example.

FIG. 5 is a schematic figure showing the measurement device 10 used in an illustrative application in accordance with embodiments. This particular application is employed for illustrative purposes only and embodiments of the present invention may also be employed for a number of other applications as will be explained.

The illustrative application shown in FIG. 5 is for assistance with the management of people who suffer from heart failure. Such conditions may have symptoms which include swelling occurring at the ankles and/or legs caused by the accumulation of blood at these parts of the body because the heart is no longer able to circulate blood around the user adequately. Such swelling can cause formations known as peripheral oedemas that can take an irregular shape.

In order to use the measurement device 10, the first part 12 is attached to the surface of a user's leg at a portion 12 near the ankle. The measurement device 10 is for measuring a change in the size and/or shape of portion 36. For example, it may measure the change in circumference of the portion 36 or a portion of the circumference. As part of the step of attaching the measurement device 10 to the portion 36, the respective first portions of the first and second parts 12, 14 may have moved relative to one another to permit the attachment. The attached state of the measurement device 10 prior to any change will be referred to as the initial condition for the purpose of describing operation of the measurement device 10. The initial condition in this example is directly related to the circumference of the portion 36. If any changes occur from this initial condition, e.g. due to swelling or reduction thereof, the circumference of the portion 36 will accordingly change.

With reference to FIG. 6a, this shows two points A and B for reference. Point A is a point on the first part 12 near an end of the second part 14 and point B is another point on the first part 12, spaced apart from point A, near an opposite end of the second part 14. Points A and B lie on the surface of the first part 12.

With reference to FIG. 6c, this shows certain component parts of the electric circuit 21 including the first element 32 and power supply schematically. The first element 32 is shown connected to a first terminal of the power supply. The resistors 32a are arranged so that adjacent resistors 32a are positioned above and below a central line respectively. A wire from the first terminal of the power supply follows a series of generally S-shaped formations as it connects the resistors 32 in series before it terminates in a free end. There is thus a first line containing a subset of the resistors 32 positioned above a second line containing another subset of the resistors 32. There is a space between the first and second lines across which the wire portions 32b each extend transversely to the lines. In embodiments, adjacent resistors 32a are spaced apart a constant distance from each other as measured with respect to the central line, which, in an embodiment is 1 mm. The total length of the first element 32 as measured along an elongate axis transverse to the wire portions 32b, e.g. the central axis, is around 45 mm.

With reference to FIG. 7a, the configuration of the determining device 20 in the initial condition is shown schematically. The second element 34 is positioned such that the electric circuit 21 is open and no current flows through the electric circuit. In this position, the second element 34 is not connected to any of the wire portions 32b. The processor is configured to operate component parts of the determining device 20 to determine a displacement between the respective portions of the first and second parts 12, 14. The processor operates the switch to the power supply and operates the current meter or circuitry to determine the current flowing through the circuit 21 and/or a resistance meter or circuitry to determine the resistance of electric circuit 21. The processor will determine there is no current because the circuit 21 is open and stores the displacement as a zero value in the memory.

The processor is configured to operate the component parts of the determining device 20 at predetermined intervals. As will be explained, the processor is configured to monitor the displacement between the respective portions of the first and second parts 12, 14 at these predetermined intervals. At each interval, the processor will determine the current flow. In embodiments, the processor may monitor the current flow differently, e.g. operating continuously over a period of time, or using a particular algorithm based on, for example, the user's daily routine. The monitoring device 10 may also be programmed by the computing device in embodiments to adopt different monitoring processes and/or switch between processes stored in the memory of the monitoring device 10.

Over time, the user may suffer from an increase in swelling at the portion 36. In which case, an increase in the relative displacement between the first portions 16, 18 may occur.

Increases in swelling can result in the shape of the portion 36 changing and/or the size, e.g. circumference, of the portion 36 changing, i.e. increasing. As this happens, the first part 12 may increase in length as shown in FIG. 6b.

In embodiments that the first part 12 is a single member, the first part 12 may stretch or extend to increase in length. In embodiments that the first part 12 includes first and second members 22, 24, these would move relative to one another and away from each other such that they are further spaced apart compared to the initial condition. In embodiments, the first part 12 may simply move relative to the second part 14 to increase the relative displacement between the first portions 16, 18.

Due to the increase in length, it can be seen that the points A and B have moved further apart as shown in FIG. 6b. The second part 14 moves in tandem with point A but it moves relative to point B so that its free end is further away therefrom. Thus, the first portion 16 of the second part 14 has moved relative to the first portion 18 of the first part. FIG. 7b shows the configuration of the determining device 20 in this condition schematically. It can be seen that the second element 34 is connected to a wire portion 32b such that a subset of the resistors 32a have been connected together in series to the second element 34. The other subset of the resistors 32a is not connected and so does not form part of the circuit created between the second element 34 and the subset of connected resistors 32a.

At the next predetermined time interval, the processor is configured to operate the component parts of the determining device 20 to determine the displacement. The power supply is switched on and a current will flow through the electric circuit because the second part 14/second element 34 has connected the subset of resistors together to form a series circuit. For example, in the embodiments represented in FIG. 7b, thirteen resistors 32a are connected together to form the circuit. The resultant current is determined by the processor. This current will be correlated to the relative displacement between first portions 16, 18 because the number of resistors connected, on which the current is dependent, is correlated to the displacement. The processor can thus determine a change in the object's size/shape has occurred and it can quantify that change as a measurement. The measurement device 10 can be used to measure the change in size in a standardised unit of measurement, e.g. in mm, in embodiments. For example, if the distance between each resistor 32a is known, then the current flow can be correlated to the total distance between the connected resistors and so used to derive a measurement in such units. In embodiments, the measurement device 10 may include a resistance meter rather than a current meter so that the total resistance of the circuit can be measured directly. In such embodiments, the total resistance would be correlated to the number of resistors connected and so the displacement measurement can similarly be calculated if the resistors are a uniform distance apart from each other. For example, in the embodiments as illustrated in FIG. 7b, the resistors are connected in series and are arranged along a series of S-shaped formations as previously described. The electric circuit includes thirteen resistors connected together and the resistors are each 1 mm apart from one another. Given the formation of the resistors, in this embodiment, the relative displacement measurement can be calculated as the total resistance divided by the resistance of each resistor and then subtracting one from the number before multiplying by 1 mm to obtain 12 mm.

Once determined, the measurement is stored in the memory and/or is sent to the computing device which has software to log and analyse the measurements. The software may identify that the swelling as occurred at a level that requires medical attention. The software may be configured to communicate through the computing device to the user directly through a notification or alarm, and/or communicate to a health professional who can decide an appropriate action.

In other periods, swelling of the portion 36 may reduce, in which case, a reduction in the relative displacement between the first portions 16, 18 may occur. In embodiments for which the first part 12 has first and second members 22, 24, these may move closer together, for example. For example, the biasing device 26 may urge the members 22, 24 together as the portion 36 reduces in size. In embodiments, the biasing device 26 may urge the second part 14 towards the first part 12 as the portion 36 reduces in size. An advantage of embodiments is that the first part 12 remains attached to the portion 36 to follow both increases and decreases in size.

Similarly, over time, the measurements obtained by the measurement device 10 can be used to identify trends that may be used to diagnose and treat the user.

Advantageously, in embodiments, the measurement device 10 can be operated without the user having to make any manual operations other than attaching the measurement device 10 to the user's body.

It will be appreciated that embodiments of the present invention may be used to measure, and/or monitor, other parts of a person's body such as the circumference of the head, neck, body core, chest, waist, limbs and extremities.

It will be appreciated that the measurement device 10 is suitable to measure and monitor, automatically if desired, changes in size or shape of other types of objects. In embodiments, the measurement device 10 may be configured for attachment to machine apparatus to monitor vibrations. It may be attached to plants or trees in embodiments. For example, the measurement device 10 may be used to measure the changes in size of a tree trunk to monitor the tree's growth. This may be advantageous for applications where a large number of plants or trees need to be monitored, i.e. in a plantation or forest respectively.

FIGS. 8a and 8b show schematically how embodiments of the present invention may be used to measure changes in size of an object having a flat surface. In embodiments, the first part 12 of the measurement device 10 may be attached by any suitable means to remain in contact with the surface of the object. In FIG. 8a, only the second part 14 and the determining device 20 are shown to illustrate this application of the embodiments. In the embodiments, the first part 12 may be a single elongate member, e.g. a rectangular shaped member, on which the second part 14 is positioned. In FIG. 8a, an initial condition is shown whereby two reference points A and B on the surface of the object are spaced apart an initial distance. In FIG. 8b, the reference points A and B have moved apart because the object has extended in a linear direction. Accordingly, the second part 14 has moved relative to a portion of the determining device a corresponding amount. In embodiments, the measurement device can measure the change in displacement between points A and B in a similar manner to that previously described in relation to the other embodiments. The features described in relation to the other described embodiments may be shared by these embodiments in the same or similar ways as will be appreciated by the skilled person.

FIGS. 9a and 9b show schematically how embodiments of the present invention may be used to measure changes in shape of an object having a surface that changes in, for example, curvature. In such embodiments, the first part 12 of the measurement device 10 may be attached by any suitable means to remain in contact with the surface of the object. In FIG. 9a, only the first part, 12, second part 14 and the determining device 20 are shown to illustrate this application of the embodiments. In FIG. 9a, an initial condition is shown whereby two reference points A and B on the surface of the object are spaced apart an initial distance. In FIG. 9b, the object has changed shape from having a relatively flat surface to one that is curved in a first direction. It can be seen that the reference points A and B have moved relative to one another due to the change of shape in the first direction. Accordingly, the free end of the second part 14 which includes the first portion 16 has moved relative to the first part 12 and a portion of the determining device a corresponding amount. In such embodiments, the measurement device can measure the change in shape by determining the relative displacement in a similar manner to that previously described in relation to the other embodiments. This has applications in measuring flexion and extension of, for example, a user's limbs or joints. The relative displacement would decrease if the object were to change shape in a second direction, e.g. change from a curved surface to a flat surface, or flexion occurring. The range of movement between a user's limbs or joints can thus be monitored or measurement over time to detect improvements or deterioration thereof to assist in, for example, physiotherapy treatments. The features described in relation to the other described embodiments may be shared by these embodiments in the same or similar ways as will be appreciated by the skilled person.

FIG. 10a is a schematic drawing of a measurement device 110 in accordance with embodiments of the present invention. Features shared in common with the previously described embodiments are denoted by the same reference number with the addition of 100. It includes a first part 112 for attachment to an object which is a single elongate member having first and second ends that are connected together by a biasing device 126. In embodiments, operative ends/operative portions (not necessarily ends) of the first part 112 may be spaced apart and the operative ends/operative portions may move further apart or closer together during use. The measurement device 110 includes a unit 140 provided on an outer surface of the first part 112 in which various component parts such as the power supply, memory and processor etc. may be located. The features described in relation to the other described embodiments may be shared by these embodiments in the same or similar ways as will be appreciated by the skilled person.

FIG. 10b is a schematic drawing of a measurement device 1010 in accordance with embodiments of the present invention. Features shared in common with the previously described embodiments are denoted by the same reference number with the addition of 1000. The measurement device 1010 has a first part 1012 for attachment to an object and no second part. Instead, the first part 1012 may be a single elongate member including first and second end portions 1050, 1052 which are configured to overlap in certain embodiments when the first part 1012 is attached to the object. The first part 1012 may be made from an elastic, or resiliently deformable, material. The first part 1012 may be opened to attach onto an object and then the elastic/resilient properties of the material cause it to be biased into a steadfast connection to the object due to the first part 1012 with no other attachment means being required. In such embodiments, the first and second end portions 1050, 1052 will move relative to one another when the object changes during use. Thus, the amount of overlap between the first and second end portions 1050, 1052 may increase or decrease depending on whether the object has increased or decreased in size. In embodiments, the first and second end portions 1050, 1052 may be connected together by a biasing device in a similar manner to that described for other embodiments. The measurement device 1010 may include a determining device 1020 having an electric circuit 1021 for determining the relative displacement of the first and second end portions 1050, 1052 in a similar manner as described in relation to the other described embodiments as will be appreciated by the skilled person. For example, the determining device 1020 may include a first element 1032 on the first end portion and a second element 1034 on the second end portion 1052 which co-operate to determine the relative displacement between the end portions. The features described in relation to the other described embodiments may be shared by these embodiments in the same or similar ways as will be appreciated by the skilled person. For example, the first part 1012 may have first and second members that are connected together and said members may include the respective end portions 1050, 1052. In embodiments, the first part 1012 may be a closed annular shape with no free ends. In such embodiments, the first and elements 1032, 1034 which co-operate with each other are provided at respective portions of the first part 1012 which move away or towards each other as the object changes.

FIG. 11 is an illustration of an advantage associated with embodiments. The figure shows an oedema in plan cross-section views with a measurement device 10 according to embodiments attached thereto expanding from a contracted to expanded condition respectively. It can be seen that the first and second parts/portions of the measurement device 10 follow the irregular shape of the oedema as the oedema changes in size and shape. In embodiments the relative displacement between the respective parts decreases as the oedema expands. It can be seen that, for embodiments including a biasing device 26, and first and second parts 12, 14, the biasing device 26 maintains the engagement of the first and second parts 12, 14 as the oedema expands and that its length increases as it does so.

Referring now to FIGS. 12a, 12b, 13a, 13b, 14a and 14b, there is shown a measurement device 210 in accordance with embodiments of the present invention. Features shared in common with the previously described embodiments are denoted by the same reference number with the addition of 200.

The measurement device 210 has a first part 212, a second part 214, a determining device 220 and a biasing device 226.

The first part 212 is a non-elastic elongate band having a first end 212a and a second end 212b. A first portion 218 of the first part 212 is provided at the first end 212a of the first part 212. A raised track or casing 240 is provided at the first portion 218 of the first part 212.

The second part 214 is a non-elastic elongate band having a first end 214a and a second end 214b. A first portion 216 of the second part 214 is provided at the first end 214a of the second part 214. An attachment device 228 is provided at the second end 214b of the second part 214.

The biasing device 226 is an elastic elongate member that has a first end 226a and a second end 226b.

The determining device 220 includes an electronic sensor 221, that is provided on the first portion 218 of the first part 212, and an inductive contact element 234 that is provided on the first portion 216 of the second part 214.

The measurement device 210 is assembled by releasably attaching the second end 212b of the first part 212 to the second end 214b of the second part 214 using the attachment device 228, which may be, for example a watch strap including leather or silicon or any other suitable material.

A first end 226a of the biasing device 226 is connected to the first portion 218 of the first part 212. A second end 226b of the biasing device 226 is connected to the first portion 216 of the second part 214.

Use of the measurement device 210 to measure and transmit changes in a wearer's ankle dimension will now be described.

The measurement device 210 is placed around a wearer's ankle. The first part 212 and the second part 214 are adjusted and fastened using the attachment device 228 such that the first portion 216 of the second part 214 overlaps at least a part of the first portion 218 of the first part 212 and the biasing device 226 is under pre-tension. In this way, a predefined return position of the first portion 216 of the second part 214 relative to the first portion 218 of the first part 212 will be achieved at the starting position of the wearer's ankle (neutral tension state).

If the wearer's ankle increases in size, the position of the first end 214a of the second part 214 moves relative to the first end 212a of the first part 212, as shown in FIG. 14b, and the biasing device 226 stretches in order to allow expansion of the measuring device 210.

Similarly, if the wearer's ankle decreases in size, the position of the first end 214a of the second part 214 moves relative to the first end 212a of the first part 212, as shown in FIG. 14a, and the biasing device 226 contracts in order to allow contracting of the measuring device 210.

The linear movement or displacement of the first portion 216 of the second part 214 relative to the first portion 218 of the first part 212 resulting from the contraction or expansion of the wearer's ankle, is converted into an electronic signal as a result of the interaction between the inductive contact element 234 on the electronic sensor components 221. The electronic sensors and transmitters 221 which detect changes in the position of the first portion 218 of the first part 212 relative to the first portion 216 of the second part 214 through measurement of the degree of movement of the inducting element 234 which is mounted on the first portion 216 of the second part 214. The resulting electronic signal denoting distance change is then transmitted wirelessly to allow remote monitoring. Mounting or electronics and inductor elements can be swapped to between the first portion 216, 218 as required or advantageous.

The provision of the raised track or casing 240 allow the first portion 216 of the second part 214 to run along the first portion 218 of the first part 212 without slippage or twisting (as shown in FIG. 12b).

The connection of the first and parts 212, 214 and the first portions 218, 216 thereof, allows the formation of at least partially overlapping, or concentric, loops.

The non-stretch or non-elastic material of the first and second parts 212, 214 ensures a 1:1 displacement of the first portion 218 of the first part 212 relative to the first portion 216 of the second part 214 during expansion or contraction in dimension of the underlying ankle tissue.

Changes in ankle dimension (perimeter) will translate into a linear distance change of first portion 218 of the first part 212 relative to the first portion 216 of the second part 214, measurable in millimetres.

In the embodiment described with reference to FIGS. 12a, 12b, 13a, 13b, 14a and 14b, the first portion 218 of the first part 212 and the first portion 216 of the second part 214 are connected by the biasing device 226, which overlaps each of the first portions 216, 218 and is secured on the external surface of segment the first and second parts 212, 214.

Alternative arrangements of the biasing device will be described with reference to FIGS. 15a, 15b, 16a, 16b, 17a and 17b.

Referring now to FIGS. 15a and 15b, there is shown a measurement device 310 in accordance with embodiments of the present invention. Features shared in common with the previously described embodiments are denoted by the same reference number with the addition of 300.

The first portion 318 of the first part 312 and the first portion 216 of the second part 314 are connected by a biasing device 326, which is secured to the measurement device 310 within an internal lumen (not shown) of the first portion 318 of the first part 312, then running through an internal lumen (not shown) within the first portion 316 of the second part 314. It will be understood that in embodiments of the invention, a combination of external fixation (as described in relation to FIGS. 12a, 12b, 13a, 13b, 14a, 14b) and internal lumen fixation (as described in relation to FIGS. 15a and 15b) may be employed.

Referring now to FIGS. 16a and 16b, there is shown a measurement device 410 in accordance with embodiments of the present invention. Features shared in common with the previously described embodiments are denoted by the same reference number with the addition of 400.

The first portion 418 of the first part 412 and the first portion 416 of the second part 414 are connected by a biasing device 426 which overlaps each of the first portions 418, 416 and is secured on the external surface of first portion 418 of the first part 412 and the first portion 416 of the second part 414. One end of the biasing device 426 is fixed to first portion 418 of the first part 412, then wrapped around a low friction element 442 allowing the biasing device 426 to double back, resulting in reduced space relative to stretch. The advantage of this configuration is that the biasing device 426 can remain within the confine of the first portion 418 of the first part 412 (which can be encapsulated) so reducing restriction on stretch due to external forces exerted on the first portion 416 of the second part 414.

Referring now to FIGS. 17a and 17b, there is shown a measurement device 510 in accordance with embodiments of the present invention. Features shared in common with the previously described embodiments are denoted by the same reference number with the addition of 500.

The first portion 518 of the first part 512 and the first portion 516 of the second part 514 are connected by a biasing device 526 which overlaps each of the first portions 518, 516 and is secured on the external surface of first portion 518 of the first part 512 and the first portion 516 of the second part 514. One end of the biasing device 526 is fixed to first portion 518 of the first part 512, then wrapped around a first low friction element 542a and a second low friction element 542b allowing the biasing device 526 to double back, resulting in reduced space relative to stretch. The advantage of this configuration is that the biasing device 526 can remain within the confine of the first portion 518 of the first part 512 (which can be encapsulated) so reducing restriction on stretch due to external forces exerted on the first portion 516 of the second part 514. Two separate biasing devices 526 a single continuous biasing device 526 can be used, giving double the elastic recoil as compared to the embodiment shown in FIGS. 16a and 16b.

Embodiments of the present invention may employ other configurations of determining device. For example, the determining device may include an electrical sensor, e.g. optical, for sensing the position of the first portion of the second part relative to the first portion of the first part to determine the relative displacement therebetween. In embodiments, the determining device may be mechanical, e.g. the determining device may simply include a gauge that is marked on one of the first or second parts so that as the respective parts move relative to one another along the gauge, a person can visually read measurements from the gauge to determine a measurement of the change in size or shape of the object. In embodiments, the first and second parts may not overlap, and/or the second part may not lie above the first part. The determining device may be configured to determine the relative displacement between the respective first portions of the first and second parts by other means e.g. optical or magnetic sensors. For example, first and second elements (e.g. light transmitter/receiver of optical sensor arrangements, or magnetic element(s)/sensing circuits of the magnetic sensor arrangements) may be provided on respective portions of the first and second parts to determine the relative displacement between the elements based on, e.g. a change in the optical signal or magnetic field when the first and second parts move. It will be appreciated that this may be employed in a similar way to embodiments (including embodiments such as those shown in FIG. 10b) for which there is no second part, and, instead, a single first part including first and second portions which move relative to one another during use. In such cases, the respective portions of the first part become closer or further apart during use when the object changes and the determining device may determine the change in the distance between them. For example, in embodiments, elements of the determining device provided on the first part may be provided at the respective first and second portions and the elements may move closer or further apart in correlation, e.g. direct proportion, to the relative displacement between the respective portions of the first part when the object changes. The first and second portions in such embodiments may not overlap or may overlap. The first and second portions may be provided at respective opposite ends of the first part in embodiments. In embodiments, the first and second portions may be positioned elsewhere.

In embodiments the determining device may include configurations of electric circuit in which at least a portion of the resistors are not connected in series and permit the increase or decrease in circuit resistance by connecting/disconnecting discrete numbers of resistors in other ways. Embodiments in which the resistance is varied by effectively adding or removing discrete resistors as the respective parts/portions of the measurement device move include one advantage in that there is substantially no drift or temperature variation in the resistance of the circuit.

In embodiments of the present invention, the measurement device may advantageously be part of a system so that changes in an object's size or shape can be remotely communicated outside of the measurement device 10 so that the relevant person or device may take appropriate action if required and/or provide notifications to the necessary person/device in response to this information.

The measuring device 10, 110, 210, 310, 410, 510, 1010 of the present invention may advantageously be used to measure ankle, foot and lower limb dimension changes caused by:

1) Heart Failure, including tricuspid valve insufficiency;
2) Lymphoedema including lymphatic system insufficiency or damage;
3) Swelling due to medication (e.g. cancer drugs);
4) Diabetes; and/or
5) Kidney dysfunction.

The measuring device 10, 110, 210, 310, 410, 510, 1010 can also be integrated into clothing or footwear, and can be worn around the bridge of the foot as well as the ankle, or incorporated into a medical clothing or footwear products.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A measurement device in the form of a band or strap configured to measure a change in one or more of a circumference or a perimeter of at least a portion of an object having a surface, the measurement device including:
    a first non-elastic elongate band arranged in a loop for attachment to the object;
    a second non-elastic elongate band arranged in a loop and having a first portion moveable relative to a first portion of the first non-elastic elongate band; the first and second non-elastic elongate bands being formed of non-compliant material and being biased towards one another by a biasing device which overlaps each of the first portions and connects the non-elastic elongate bands together, the measurement device further comprising a determining device for determining a displacement of the first portion of the second non-elastic elongate band relative to the first portion of the first non-elastic elongate band caused by the object changing the one or more of the circumference or perimeter of at least a portion of the object;
    wherein the displacement is for use in measuring the change in the one or more of the circumference or the perimeter of the object.

2. A measurement device according to claim 1, wherein at least the first portion of the first non-elastic elongate band is positioned above or below the first portion of the second non-elastic elongate band.

3. A measurement device according to claim 1, wherein the determining device is provided on at least one of the first and second non-elastic elongate bands.

4. A measurement device according to claim 1, wherein the first and second non-elastic elongate bands are connected.

5. A measurement device according to claim 1, wherein the second non-elastic elongate band has a second portion which is fixed against movement relative to the first non-elastic elongate band, or wherein the first portion of the second non-elastic elongate band is slidingly connected to the first non-elastic elongate band.

6. A measurement device according to claim 1, wherein at least the first portion of the second non-elastic elongate band is biased towards the first non-elastic elongate band and/or the first and second non-elastic elongate bands are biased towards engagement with the object when the measurement device is attached thereto.

7. A measurement device according to claim 5 wherein at least the first portion of the second non-elastic elongate band is biased towards engagement with the first non-elastic elongate band.

8. A measurement device according to claim 1, comprising a raised track or casing provided at the first portion of the first non-elastic elongate band to allow the first portion of the second non-elastic elongate band to run along the first portion of the first non-elastic elongate band without slippage or twisting.

9. A measurement device arranged in the form of a band or strap for measuring a change in one or more of a circumference or a perimeter of at least a portion of an object having a surface, the measurement device including:
    a first non-elastic elongate band for attachment to the object, wherein the first non-elastic elongate band is arranged in a loop and includes a first non-compliant portion and a second non-compliant portion which are configured to permit relative movement between them when the object changes the one or more of the circumference or perimeter of at least a portion of the object;
    a determining device for determining a relative displacement of the first and second portions caused by the object changing,
    wherein the displacement is for use in measuring the change in one of more of the circumference or the perimeter of the object.

10. A measurement device according to claim 1, including one or more of the following:
    a) the respective first portions of the first and second non-elastic elongate bands, are biased against relative movement between them; and
    b) the respective portions of the first and second non-elastic elongate bands, at least partially overlap.

11. A measurement device according to claim 1, wherein the determining device includes a first element provided on one of the first and second non-elastic elongate bands/portions, and a second element provided on the other of the first and second non-elastic elongate bands/portions, wherein the first and second elements may cooperate to determine the displacement.

12. A measurement device according to claim 1, wherein the determining device includes an electric circuit connectable to a power supply of the measurement device and the electric circuit has a variable resistance which increases or decreases in correlation to the displacement.

13. A measurement device according to claim 12, wherein the determining device includes an electric circuit connectable to a power supply of the measurement device and the electric circuit has a variable resistance which increases or decreases in correlation to the displacement, and further wherein the first and second elements cooperate to form the electric circuit.

14. A measurement device according to claim 13, wherein the electric circuit includes a plurality of resistors, and wherein the first and second elements co-operate to vary the number of resistors connected in the electric circuit when the first portion of the second non-elastic elongate band moves relative to the first portion of the first non-elastic elongate band such that the resistance of the electric circuit is correlated to the displacement.

15. A measurement device according to claim 1, wherein the first non-elastic band/portion, and/or second non-elastic band/portion, are deformable to follow the surface of the object as it changes during use, the non-elastic bands/portions are resiliently deformable, and/or wherein the first non-elastic band includes an engagement surface, which, in use, remains in steadfast engagement with the surface of the object as the object changes.

16. A measurement device according to claim 1, wherein the first non-elastic elongate band is releasably attachable to the object, and/or includes an attachment device for attaching the first non-elastic elongate band to the object.

17. A measurement device according to claim 1, wherein the measurement device is configured as a user wearable device for attachment to a portion of a user's body to measure changes in said portion, and/or wherein the measurement device includes one or more or all of the following features:
   a) a processor;
   b) memory for storing instructions and/or data for processing by the processor; and
   c) communication link for communicating with a computing device,
   wherein features a) to c) are arranged to operate the determining device to obtain the displacement, and/or communicate said displacement to a computer device at pre-determined intervals and/or as instructed by the computing device.

18. A measurement device in the form of a band or strap for measuring a change in one or more of the circumference or perimeter of at least a portion of an object having a surface, the device including:
   a first part arranged in a loop for attachment to the object;
   a second part arranged in a loop and having a first portion moveable relative to a first portion of the first part;
   a raised track or casing provided at the first portion of the first part to allow the first portion of the second part to run along the first portion of the first part without slippage or twisting, and
   a determining device for determining a displacement of the first portion of the second part relative to the first portion of the first part caused by the object changing the one or more of the circumference or perimeter of at least a portion of the object;
   wherein the displacement is for use in measuring the change in the one or more of the circumference or perimeter of the object.

19. A measurement device according to claim 1, for measuring a change in one or more of the circumference or perimeter of at least a portion of a user's ankle, foot or lower limb.

20. A measurement device according to claim 19, wherein the measurement device comprises an ankle bracelet.

* * * * *